United States Patent [19]

Vladuchick

[11] 4,094,985

[45] June 13, 1978

[54] FUNGICIDAL ISOTHIAZOLES

[75] Inventor: Susan Anne Vladuchick, Newark, Del.

[73] Assignee: E. I. Du Pont de Nemours and Company, Wilmington, Del.

[21] Appl. No.: 777,881

[22] Filed: Mar. 17, 1977

Related U.S. Application Data

[63] Continuation-in-part of Ser. No. 731,981, Oct. 13, 1976, abandoned, which is a continuation-in-part of Ser. No. 625,132, Oct. 23, 1975, abandoned.

[51] Int. Cl.$^2$ .................. A61K 31/425; C07D 513/04
[52] U.S. Cl. ................................. 424/270; 260/302 F
[58] Field of Search ..................... 260/302 F; 424/270

[56] References Cited

PUBLICATIONS

Feher et al., Tetrahedron Lett; 1971, (24), 2125–2126.
Feher et al., Z. Naturforsch. B, 1972, 27(8), 1006–1007.

*Primary Examiner*—R. J. Gallagher

[57] ABSTRACT

Compounds of the formula

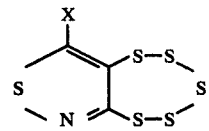

wherein
X is cyano or

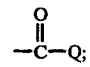

Q is Cl, $-OR_1$, $-SR_1$ or $-NR_2R_3$;
$R_1$ is hydrogen or alkyl of 1–2 carbon atoms,
$R_2$ is hydrogen or methyl; and
$R_3$ is hydrogen, alkyl of 1–4 carbon atoms or phenyl, with the proviso that (a) when $R_2$ is hydrogen, $R_3$ is hydrogen or alkyl of 1–3 carbon atoms or phenyl and (b) when Q is $-SR_1$, $R_1$ is not hydrogen, are useful as fungicides and reaction intermediates. These compounds may be prepared by reacting substituted 3,4-dimercaptoisothiazole salts with sulfur monochloride.

18 Claims, No Drawings

FUNGICIDAL ISOTHIAZOLES

CROSS-REFERENCE TO RELATED APPLICATION

This application is a continuation-in-part of my copending application Ser. No. 731,981, filed Oct. 13, 1976, now abandoned, which is a continuation-in-part of my copending application Ser. No. 625,132, filed October 23, 1975, now abandoned.

BACKGROUND OF THE INVENTION

This invention relates to isothiazolo[3,4-f][1,2,3,4,5]pentathiepines substituted in the 3-position with various radicals and the process of preparing them. These compounds are useful as agricultural and industrial fungicides or reaction intermediates.

The applicant is aware of no references which teach the compounds of this invention or suggest their utility. Feher et al. published two articles dealing with pentathiepine fused ring compounds; Z. Naturforsch, 27b, p. 1006-7 (1972) and Tetrahedron Letters, (24), p. 2125-6 (1971). These references disclose the reaction of various sulfur chlorides with dimercapto-substituted compounds to produce heterocyclic sulfur compounds including pentathiepines. However, neither reference teaches making an isothiazolopentathiepine and neither reference suggests any utility for any of the compounds described.

SUMMARY OF THE INVENTION

Compounds of the formula

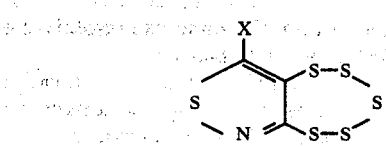

wherein
X is cyano or

$-\overset{O}{\underset{\|}{C}}-Q$;

Q is Cl, $-OR_1$, $-SR_1$ or $-NR_2R_3$;
$R_1$ is hydrogen or alkyl of 1–2 carbon atoms;
$R_2$ is hydrogen or methyl; and
$R_3$ is hydrogen, alkyl of 1–4 carbon atoms or phenyl,
with the proviso that (a) when $R_2$ is hydrogen, $R_3$ is hydrogen or alkyl of 1–3 carbon atoms or phenyl and (b) when Q is $-SR_1$, $R_1$ is not hydrogen, are agricultural and industrial fungicides or novel intermediates for the preparation of these fungicides.

The fungicides of this invention may be applied to plants, fabric, leather, wood and the like for both preventive and in some cases eradicant fungicidal activity. The phrase "application to plants" as used herein is meant to encompass direct application to the plants as well as application to soil, plant parts or seeds.

The active compounds of this invention are generally applied as compositions, i.e., formulations, consisting essentially of the active ingredient admixed with a surfactant or inert diluent or both. The phrase "consisting essentially of" as used herein does not exclude the presence of unspecified items which do not prevent the advantages of this invention from being realized.

Most of the compounds of this invention can be synthesized according to the following reaction

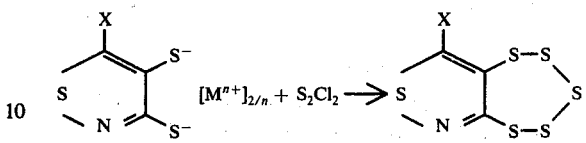

where X can be —CN or

$-\overset{O}{\underset{\|}{C}}-Q$,

Q can be $OR_1$, $SR_1$ or $NR_2R_3$, $R_1$, $R_2$ and $R_3$ are defined as above, $M^{n+}$ is a metal cation and n is the valence of the metal cation, with the proviso that (a) when $R_2$ is hydrogen, $R_3$ is hydrogen or alkyl of 1–3 carbon atoms or phenyl and (b) when Q is $-SR_1$, $R_1$ is not hydrogen.

All of the compounds of this invention can be made by first synthesizing isothiazolo[3,4-f][1,2,3,4,5]pentathiepine-3-carbonitrile according to the reaction above and then converting this product to the desired compound. Isothiazolo[3,4-f][1,2,3,4,5]pentathiepine-3-(carboxylic acid) and the acid chloride of this compound are particularly useful intermediates for preparation of the esters and amides of this invention. These intermediates are novel.

DETAILED DESCRIPTION OF THE INVENTION

Of the compounds described above, those of the formula

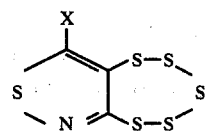

where X is —CN or

$-\overset{O}{\underset{\|}{C}}-Q$,

Q is $-NR_2R_3$ and $R_2$ and $R_3$ are as defined above are preferred. More preferred are those compounds where X is —CN or

$-\overset{O}{\underset{\|}{C}}-Q$,

Q is $-NR_2R_3$ and $R_3$ is hydrogen or alkyl of 1–3 carbon atoms. Specifically preferred are isothiazolo[3,4-f][1,2,3,4,5]pentathiepine-3-carbonitrile, (mp 141°–142° C), isothiazolo[3,4-f][1,2,3,4,5]pentathiepine-3-carboxamide (mp 170° C) and isothiazolo[3,4-f][1,2,3,4,5]pentathiepine-3-[N-(1-methylethyl)carboxamide] (mp 153°–154° C).

The synthesis of the compounds of this invention is exemplified by the following reaction

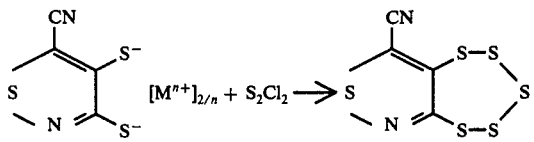
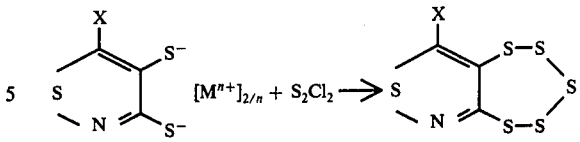

This reaction is conducted in an aprotic solvent such as an ether, tetrahydrofuran, benzene, chloroform, or acetonitrile. This list is not intended to exclude other useful aprotic solvents. 1,2-Dimethoxyethane is a preferred solvent.

The order of addition of reactants is not critical, but better yields are obtained by adding $S_2Cl_2$ to a stirred suspension of the dimercaptoisothiazole salt. The ratio of reactants is not critical and can range from 1 part of sulfur monochloride to 10 parts of the dimercaptoisothiazole salt to 10 parts $S_2Cl_2$ to 1 part salt. The preferred ratio is from 1:1 to 1.1:1.

The temperature and pressure at which the reaction is run are not critical. Temperatures can range from $-80°$ C to $50°$ C and pressures from 0.01 to 100 atmospheres. The preferred temperature range is $-5$-$+5°$ C and the preferred pressure is ambient pressure.

The dimercapto salt is prepared by reacting 1,2-dimercaptomaleonitrile sodium salt with sulfur in an alcohol solvent at a temperature of at least $50°$ C. The addition of a catalyst such as tetracyano-1,4-dithiin is preferred. The catalyzed reaction requires two to twelve hours with two to four hours usually being sufficient. Mole ratios of 1–1.2 gram atoms of sulfur and 0.1 mole catalyst per mole of dimercaptomaleonitrile salt give adequate yields and do not require subsequent removal of unreacted starting material.

1,2-Dimercaptomaleonitrile sodium salt is produced by the reaction of carbon disulfide and sodium cyanide as described in Bähr et al., Chem. Ber., 88, 1771 (1955) and 90, 438 (1957). The reaction of this product with sulfur proceeds in alcohol solvents such as methanol or ethanol, or in dipolar aprotic solvents such as tetrahydrofuran. Ethanol is preferred. The reaction is carried out at $50°$-$150°$ C, preferably at the reflux temperature of the reaction mixture.

Other salts of the 1,2-dimercaptomaleonitrile may be used in place of the disodium salt. These salts are prepared from the disodium salt by the procedure of Simmons et al., J. Amer. Chem. Soc., 84, 4756 (1962) for the preparation of the bis(tetramethylammonium) salt, or by ion exchange on a column of a suitable resin. Similarly, other metal salts of the 3,4-dimercaptoisothiazole-5-carbonitrile can be prepared and used in the reaction with sulfur monochloride in the preparation of the compounds of this invention. However, the disodium salt is preferred in both reactions for ease of preparation and handling.

Just as other metal salts can be used in place of the sodium salt in the reaction described above, the carbonitrile substituent on the isothiazole starting material can be replaced by an acid group, ester group, a thioester group, or an amide group, depending on the final product desired. Thus, the reaction shown above can be written more generally:

where X is —CN or

Q is $-OR_1$, $-SR_1$ or $-NR_2R_3$;
$R_1$ is hydrogen or alkyl of 1-2 carbon atoms;
$R_2$ is hydrogen or methyl;
$R_3$ is hydrogen or alkyl of 1-4 carbon atoms or phenyl;
$M^{n+}$ is a metal cation; and
$n$ is the valence of the cation, with the proviso that (a) when $R_2$ is hydrogen, $R_3$ is hydrogen or alkyl of 1–3 carbon atoms or phenyl, and (b) when Q is $-SR_1$, $R_1$ is not hydrogen.

The same reactions for converting the carbonitrileisothiazole to isothiazoles with other substituents can be used to convert isothiazolo[3,4-f][1,2,3,4,5]pentathiepine-3-carbonitrile to other isothiazolopentathiepines within the scope of this invention. Thus, some of the compounds of this case can be made either by first making the properly substituted dimercaptoisothiazole salt and reacting it with sulfur monochloride or by making isothiazolo[3,4-f][1,2,3,4,5]pentathiepine-3-carbonitrile and converting it to the desired end product. For these compounds the carbonitrile reactions described below refer to both the dimercaptoisothiazole salts and to the isothiazolopentathiepines.

Carbonitriles are converted to the corresponding unsubstituted carboxamides by reacting the carbonitrile compound with an excess of a mineral acid such as concentrated sulfuric acid. The temperature of the reaction is maintained between $0°$-$50°$ C. The resulting reaction mixture is stirred for several hours and the product is isolated by pouring the reaction mixture into water and filtering the mixture.

Carbonitriles are converted to the acid by first making the carboxamide as above, dissolving it in an acid having a PKa of 5 or less, cooling the mixture to $0°$-$10°$ C and treating it with an excess, preferably 2–3 molar equivalents, of an alkali or alkaline earth metal nitrite. The reaction mixture is warmed to $50°$-$100°$ C and the product isolated by pouring the reaction mixture into ice water and filtering. For economic reasons, hydrochloric or sulfuric acid and sodium nitrite are preferred in this reaction. Alternate sources of nitrous acid such as an organic nitrite or nitrogen oxides can be used in this reaction if desired.

Isothiazolo[3,4-f][1,2,3,4,5]pentathiepine-3-(carboxylic acid) can be converted to the corresponding carbonyl chloride by reaction with a chlorinating reagent such as thionyl chloride or oxalyl chloride in a suitable solvent such as benzene, hexane, dichloromethane, chloroform or excess thionyl chloride or oxalyl chloride. N,N-dimethylformamide catalyzes acid chloride formation. The product is isolated by evaporating the solvent. The carbonyl chloride compound serves as an intermediate for making esters, thioesters and substituted carboxamides within the scope of this invention.

This pentathiepine carbonyl chloride can be converted to a carboxamide,

where $R_2$ and $R_3$ are defined as above by reaction with an excess of the appropriate amine with external cooling, if necessary. Suitable solvents include benzene, hexane, dichloromethane, chloroform or the excess amine. The product amides can be isolated by evaporating the solvent or pouring the reaction mixture into water and filtering the mixture.

Esters are made by reacting the pentathiepine carbonyl chloride with an alcohol or mercaptan of the formula $R_1OH$ or $R_1SH$ where $R_1$ is defined as above. This reaction is carried out in a solvent such as benzene or dichloromethane. The product is isolated by evaporating the solvent or pouring the reaction mixture into water and filtering the mixture. With mercaptans the reaction proceeds in the absence of solvents.

Alternatively, the esters of this invention can be made from the corresponding pentathiepine or isothiazole carboxylic acid by reacting these acids with an alcohol or mercaptan in the presence of a small amount of a mineral acid such as sulfuric or hydrochloric acid.

The compounds of this invention have outstanding activity for the prevention and control of a wide spectrum of diseases caused by various pathogenic fungi. The compounds are not only effective as preventive fungicides, but also exert a strong curative effect, that is, they can be applied after infection has been established in the host plant or material, during the incubation period, and can stop the development of the disease. This quality is especially desirable in agricultural applications because a grower can follow a disease forecasting system and wait for weather conditions favorable to plant infection before applying the chemical control agent. This can significantly reduce the number of applications and reduce waste.

The fungicides of this invention have a broad spectrum of activity against fungus pathogens which differ greatly. Some of the pathogens susceptible to control are Ascomycetes represented by *Venturia inaequalis*, the cause of apple scab, and the powdery mildew fungi *Erysiphe spp.*; others are Basidiomycetes represented by *Gymnosporangium juniperi-virginianae*, and other rust fungi; others are Phycomycetes represented by *Phytophthora infestans*, the cause of potato and tomato late blight and Fungi Imperfecti represented by *Cercospora beticola*.

The fungicides of this invention have a broad spectrum of activity against fungi which rot fabric, leather, and wood. These fungi are in a dynamic relationship in soils. Items treated with the fungicides of this invention resist decay even when buried in moist soil.

Rates for application to seeds, tubers, bulbs or other plant reproductive parts, range from 10 to 1000 grams of active compound of this invention per 50 kilograms of planting material treated. Applications are made from dusts, slurries or solutions.

Rates for application of the compounds of this invention to foliage, stems and fruit of living plants range from 0.1 to 10 kilograms of active ingredient per hectare or 1 to 1000 ppm, preferably 0.5 to 5 kg/Ha or 5 to 500 ppm. The optimum amount within this range depends upon a number of variables which are well known to those skilled in the art of plant protection. These variables include, but are not limited to, the disease to be controlled, weather conditions expected, the type of crop, stage of development of the crop, and the interval between applications. Applications within the range given may need to be repeated one or more times at intervals of 1 to 60 days. Applications are made from dusts, slurries or solutions.

Rates for application to fabric, leather, or wood range from 0.1 to 5% based on chemical weight per dry weight of material to be treated. The optimum amount varies within this range depending on desired degree and length of protection under various conditions conductive to rotting.

Useful formulations of the compounds of Formula I can be prepared in conventional ways. They include dusts, solutions, suspensions, emulsions, wettable powders, emulsifiable concentrates and the like. Many of these may be applied directly to the plants. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following aproximate proportions:

|  | Percent by Weight | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

For industrial applications many of the same compositions may be used. For example, wettable powders and aqueous suspensions may be utilized in aqueous media. Solutions in organic solvents well under 5% by weight active ingredient, even below 1% active, are useful in treating wood and other organic materials.

Typical solid diluents are described in Watkins et al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

Agricultural compositions, i.e., formulations, which contain the compound of this invention as active ingredient may also contain other active ingredients such as conventional insecticides, miticides, bactericides, nematicides, fungicides, or other agricultural chemicals such as fruit set agents, fruit thinning compounds, fertilizer ingredients, and the like. The additional agricultural chemicals are employed in mixtures or combinations in amounts ranging from one-tenth to twenty times that of the compound or compounds of this invention. The proper choice of amounts is readily made by one skilled in the art of protecting plants from pest depredations. The following are illustrative of the agricultural chemicals that may be included in compositions or added to sprays containing one or more of the active compounds of this invention:

bis(dimethylthiocarbamoyl)disulfide; or tetramethylthiuram disulfide (thiram);
metal salts of ethylenebisdithiocarbamic acid or propylenebisdithiocarbamic acids, e.g. manganese, zinc, iron and sodium salts (maneb or zineb);
n-dodecylguanidine acetate (dodine);
N-(trichloromethylthio)phthalimide (folpet);
N-[(trichloromethyl)thio]-4-cyclohexene-1,2-dicarboximide (captan);
cis-N-[(1,1,2,2-tetrachloroethyl)thio]-4-cyclohexene-1,2-dicarboximide (captafol);
2,4-dichloro-6-(o-chloroanilino)-S-triazine (anilazine);
3,3'-ethylenebis(tetrahydro-4,6-dimethyl-2H-1,3,5-thiadiazine-2-thione), (milneb);
triphenyltin hydroxide (fentin hydroxide);
triphenyltin acetate (fentin acetate);
N'-dichlorofluoromethylthio-N,N-dimethyl-N'-phenylsulfamide (dichlorofluanid);
tetrachloroisophthalonitrile (chlorothalonil);
tribasic copper sulfate;
fixed copper;
sulfur;
methyl 1-(butylcarbamoyl)-2-benzimidazolecarbamate (benomyl);
methyl 2-benzimidazolecarbamate (carbendazim);
1,2-bis(3-methoxycarbonyl-2-thioureido)benzene (methyl thiophanate);
2-cyano-N-(ethylcarbamoyl)-2-methoxyiminoacetamide.

The agricultural chemicals listed above are merely exemplary of compounds that may be mixed with the active compounds of this invention to broaden the spectrum of disease control.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084) and J. E. Browning, "Agglomeration", *Chemical Engineering,* Dec. 4, 1967, pp. 147ff., and "Perry's Chemical Engineer's Handbook", 4th Edn., McGraw-Hill, N.Y., 1963, pp. 8-59ff.

This invention is further illustrated by the following Examples.

EXAMPLE 1

Isothiazolo[3,4-f][1,2,3,4,5]pentathiepine-3-carbonitrile

A mixture of 1,2-dimercaptomaleonitrile disodium salt (18.6 g, 0.1 mol), sulfur (4.0 g, 0.125 g-atom) and tetracyano-1,4-dithiin (2.16 g, 0.01 mol), *J. Amer. Chem. Soc.* 84, 4746 [1962] and ethanol (250 ml) was heated at reflux for 2 hours. The mixture was filtered hot and cold successively to remove sulfur, and the filtrate was evaporated to leave 10.2 g of yellow solid, 3,4-dimercaptoisothiazole-5-carbonitrile disodium salt.

A solution of 14 ml of $S_2Cl_2$ (0.153 mol) in 100 ml of 1,2-dimethoxyethane was added at the rate of 1 ml/min to a stirred suspension of 32.4 g 3,4-dimercaptoisothiazole-5-carbonitrile disodium salt in 2 liters of 1,2-dimethoxyethane. The reaction mixture was maintained at 0° C. After the addition was complete, sodium chloride was removed by filtration. The solvent was vacuum distilled to give 36.1 g of isothiazolo[3,4-f][1,2,3,4,5]pentathiepine-3-carbonitrile. Low temperature recrystallization from chlorobutane gave 22 g of purified product, m.p. 141°-142° C, a 55% yield based on 3,4-dimercaptoisothiazole-5-carbonitrile disodium salt; mass spectrum:m/e 267 (M)$^+$ and 235 (M-S)$^+$.

Anal. Calcd. for $C_4N_2S_6$: C, 17.9; N, 10.44; S, 71.66; m/e 267.8386 Found: C, 19.6; N, 10.1 19.3 S, 71.3; m/e 267.8447

EXAMPLE 2

Isothiazolo[3,4-f][1,2,3,4,5]pentathiepine-3-carboxamide

Three grams of isothiazolo[3,4-f][1,2,3,4,5]pentathiepine-3-carbonitrile was added to 75 ml of chilled concentrated sulfuric acid. The mixture was stirred at room temperature for two hours and then poured into ice water and filtered to produce 3.2 g of isothiazolo[3,4-f][1,2,3,4,5]pentathiepine-3-carboxamide, mp 170° C; IR: $\lambda_{max}^{KBr}$ 2.98, 3.18, 6.05, 6.33 and 6.74 μm.

Anal. Calcd. for $C_4N_2H_2OS_6 \cdot H_2O$: C, 15.8; H, 1.32 N, 9.2; S, 63.2 Found: C, 15.5; H, 1.28 15.9; 1.32 N, 9.6; S, 63.2, 9.1; 63.5

EXAMPLE 3

Isothiazolo[3,4-f][1,2,3,4,5]pentathiepine-3-(carboxylic acid)

Isothiazolo[3,4-f][1,2,3,4,5]pentathiepine-3-carboxamide (1.55 g, 0.005 mol) was dissolved in 15.4 ml of warm concentrated sulfuric acid. The solution was cooled to 15°-20° C and a solution of 1.55 g of sodium nitrite in 8 ml of water was slowly added. The resulting suspension was warmed to 70° C until nitrogen evolution ceased. The mixture was cooled and poured into ice water. A wet cake yellow product, isothiazolo[3,4-f][1,2,3,4,5]pentathiepine-3-(carboxylic acid), was collected by filtration. The acid was separated from unreacted amide by extraction with 5% sodium bicarbonate solution and acidification of the resulting extract.

Calcd. for $C_4NS_6O_2H$: C, 16.7; N, 4.88; H, 0.35 Found: C, 16.9; N, 5.5; H, 0.64 16.6, 5.6, 0.63

EXAMPLE 4

Isothiazolo[3,4-f][1,2,3,4,5]pentathiepine-3-(carboxylic acid)

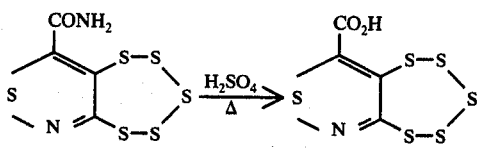

200 g of concentrated sulfuric acid was placed in a 2-liter 3-neck flask equipped with a mechanical stirrer, condenser, thermometer, nitrogen cap, and an outlet leading to a 20% aqueous potassium hydroxide trap. Isothiazolo[3,4-f][1,2,3,4,5]pentathiepine-3-carboxamide (21.0 g, 0.078 mol) was added over 2 min. The mixture was warmed slowly to 70° C to give a cloudy orange-red solution. This was cooled to 0° C, and treated with a solution of sodium nitrite (20 g, 0.29 mol) in water (10 ml) over 1.5 h at 5°–10° C. The temperature of the mixture was slowly raised to 87° C; nitrogen evolution began at 40° C, and was controlled by regulating the temperature. The mixture was poured over 1 liter of stirred ice; after the ice had melted, the mixture was filtered, and the filter cake was washed well with water to give 10.20 g (0.036 mole, 46%) of the crude carboxylic acid. A one-gram sample was recrystallized from 15 ml of acetic acid, recovery 0.70 g of yellow isothiazolo[3,4-f][1,2,3,4,5]pentathiepine-3-(carboxylic acid) with mp 159°–165° C; mass spectrum: m/e 286 (M)+, 242 (M-CO$_2$)+ 190 (M-S$_3$)+ and 132 (M-CNS$_4$)+.

Anal. Calcd. for C$_4$HO$_2$NS$_6$: m/e 286.8331 Found: m/e 286.8328.

The preparation was repeated with 83.1 g (0.31 mol) of amide, 780 g of sulfuric acid and 78.0 (1.13 mol) of sodium nitrite in 390 ml of water to give 23.90 g (0.084 mol, 27%) of carboxylic acid.

EXAMPLE 5

Isothiazolo[3,4-f][1,2,3,4,5]pentathiepine-3-(N,N-dimethylcarboxamide)

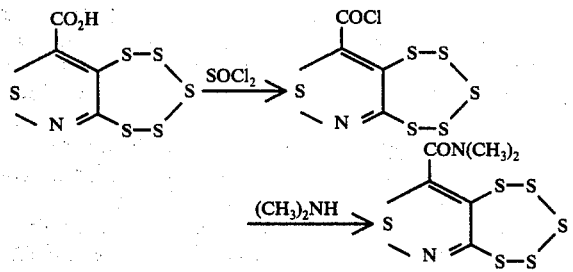

A. Isothiazolo[3,4-f][1,2,3,4,5]pentathiepine-3-(carbonyl chloride) (thionyl chloride method)

A 500-ml RB flask equipped with a magnetic stirrer, reflux condenser, and nitrogen cap was charged with benzene (200 ml), isothiazolo[3,4-f][1,2,3,4,5]pentathiepine-3-(carboxylic acid) (5.0 g, 0.0174 mol), thionyl chloride (1.50 ml) and N,N-dimethyl formamide (10 drops). The mixture was stirred at reflux for 1.5 h to give an orange solution of the acid chloride which was used directly for the preparation of the amide.

B. Isothiazolo[3,4-f][1,2,3,4,5]pentathiepine-3-(N,N-dimethyl-carboxamide)

A solution of 2.2 ml (0.033 mol) of anhydrous dimethylamine in benzene (50 ml) was stirred at 5°–7° C. and treated dropwise with the benzene solution of the acid chloride from Part A, similarly cooled to 5° C After the mixture had stirred at 7° C. for 1 h, it was allowed to come to 25° C and 2 g of dimethylamine hydrochloride was removed by filtration. The filtrate was evaporated to leave 5.4 g of the crude amide as an orange-yellow gum. This was dissolved in dichloromethane and chromatographed on 80 g of SilicAR CC-7 Special adsorbent using dichloromethane, 1:1 dichloromethane-ethyl acetate, and ethyl acetate as successive eluents. The later fractions gave 3.08 g (0.011 mol, 63%) of purified amide. This material was dissolved in 1-chlorobutane and the solution was cooled to −78° C and filtered. The filtrate was evaporated to dryness, and the residue of colorless isothiazolo[3,4-f][1,2,3,4,5]pentathiepine-3-(N,N-dimethyl-carboxamide) was stored under nitrogen. The pure product has mp 102°–105° C; IR: $\lambda_{max}^{KBr}$ 3.41 (w), 6.10 (s) and 6.66 μm; and mass spectrum: m/e 281 (M)+, 217 (M-S$_2$)+ and 205 (M-S(CH$_3$)$_2$N)+.

Anal. Calcd. for C$_6$H$_6$N$_2$OS$_6$: C, 25.5; H, 2.14; N, 9.92; S, 56.75; m/e 281.9083 Found: C, 24.0; H, 2.07; N, 8.84; 23.5 2.19 8.75 S, 61.12; m/e 281.9116

EXAMPLE 6

Isothiazolo[3,4-f][1,2,3,4,5]pentathiepine-3-[N-(1-methylethyl)carboxamide]

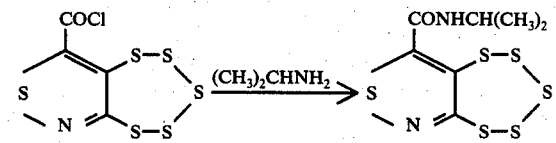

The method of Example 5 was used, substituting 2.81 ml (0.033 mol) of isopropylamine for the dimethylamine. The crude orange gummy product was chromatographed on 80 g of SilicAR CC-7 Special adsorbent using benzene, 1:1 benzene: chloroform, and benzene as successive eluents. The later fractions gave purified product which was recrystallized from heptane with Darco G-60 treatment. Isothiazolo[3,4-f][1,2,3,4,5]pentathiepine-3-N-[(1-methylethyl)carboxamide] forms colorless crystals with mp 153°–154° C; IR: $\lambda_{max}^{KBr}$ 3.05 (NH), 3.35, 3.40, 6.17 and 6.43 μm (CONH); NMR (CDCl$_3$-TMSi): δ1.3 (d) (CH$_3$)$_2$CH and 4.2 ppm (q) NH; and mass spectrum: m/e 295 (M)+, 263 (M-S)+, 221 and 205.

Anal. Calcd. for C$_7$H$_8$N$_2$OS$_6$: C, 25.6; H, 2.44; N, 8.54; S, 58.54; m/e 295.9240 Found: C, 26.4; H, 2.36; N, 8.62; 26.3, 2.41, 8.64 S, 58.0; m/e 295.9240

EXAMPLE 7

Methyl Isothiazolo[3,4-f][1,2,3,4,5]pentathiepine-3-carboxylate

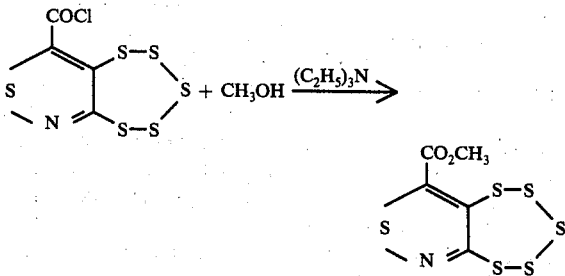

Isothiazolo[3,4-f][1,2,3,4,5]pentathiepine-3-(carbonyl chloride), prepared by the method of Example 5A, was added dropwise to a solution of methanol (0.70 ml, 0.56 g, 0.0174 mol) in benzene (50 ml) at 5° C under nitrogen. A few minutes after the addition of the acid chloride was begun, a solution of triethylamine (2.50 ml, 1.80 g, 0.0174 mol) in benzene (150 ml) was added dropwise. The addition was complete after 45 min at 5° C; the mixture was stirred at 25° C for 3 h, and then it was filtered. The filtrate was evaporated to give 5.30 g of yellow crystalline solid which was chromatographed on 100 g of SilicAR CC-7 Special adsorbent using benzene, 9:1, 5:1, 4:1, 1:1 and 1:3 benzene: chloroform mixtures as successive eluents. Methyl isothiazolo [3,4-f][1,2,3,4,5]pentathiepine-3-carboxylate was recrystallized from heptane; it is a yellow solid with mp 68°–72° C; IR: $\lambda_{max}^{KBr}$ 5.76 μm ($CO_2CH_3$); NMR ($CDCl_3$-TMSi): δ 3.95 (s) $CO_2CH_3$; and mass spectrum: m/e 300 $(M)^+$, 178 $(M-CO_2CH_3-S_2)^+$ and 146 $(M-S_2CN)^+$.

Anal. Calcd. for $C_5H_3NO_2S_6$: C, 19.9; H, 1.00; N, 4.65; S, 63.8; m/e 300.8488 Found: C, 18.15; H, 1.09; N, 4.34 18.10, 1.12, 4.33 S, 66.81; m/e, 300.8505

EXAMPLE 8A

Isothiazolo[3,4-f][1,2,3,4,5]pentathiepine-3-carbonyl chloride) (oxalyl chloride method)

A mixture of isothiazolo [3,4-f][1,2,3,4,5]pentathiepine-3-(carboxylic acid) (1.5 g, 0.005 mol), benzene (20 ml) and N,N-dimethylformamide (2 drops) was stirred under nitrogen and treated with oxalyl chloride (5 ml). Samples were quenched in methanol and the progress of the reaction was followed by thin layer chromatography ($SiO_2$-$CHCl_3$). The mixture was evaporated to dryness after 1 h at 25° C. Benzene was added to the residue, and the mixture was evaporated again. The residue was dissolved in more benzene and filtered under nitrogen; the filtrate was evaporated and pumped to dryness (0.1 mm) to leave the yellow partly crystalline acid chloride.

EXAMPLE 8B

Ethyl Isothiazolo[3,4-f][1,2,3,4,5]pentathiepine-3-(S-thiocarboxylate)

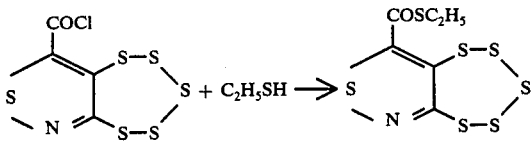

The procedure of Example 8A was used with 0.7 g of isothiazolo[3,4-f][1,2,3,4,5]pentathiepine-3-(carboxylic acid). The crude acid chloride was treated with a solution of ethanethiol (5 ml) in dichloromethane (15 ml) at 25° C for 3 h; no starting material remained by thin layer chromatography ($SiO_2$ – $CHCl_3$). The solvent was evaporated and the residue was distributed between dichloromethane and water. The water layer was washed once with dichloromethane, and the combined dichloromethane extracts were dried over magnesium sulfate, treated with Darco G-60, filtered, and evaporated to dryness. The residue of ethyl isothiazolo[3,4-f][1,2,3,4,5]pentathiepine-3-(S-thiocarboxylate) of 61% purity (HPLC) has IR: νmax 1640 and 1665 cm$^{-1}$ ($COSC_2H_5$); and NMR: signals characteristic of an ethyl group. The reaction was also done in the absence of dichloromethane solvent.

EXAMPLE 9

Isothiazolo[3,4-f][1,2,3,4,5]pentathiepine-3-(N-methyl-N-butyl-carboxamide)

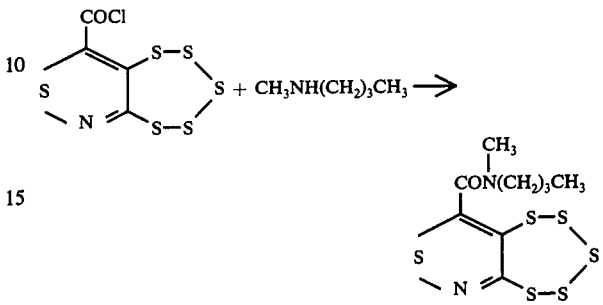

The method of Example 8A was used to prepare the acid chloride from 4.7 g of carboxylic acid. The method of Example 5B was employed using a solution of 4.2 ml of N-methylbutylamine in benzene (20 ml) in place of dimethylamine. The crude oily product (4.13 g) was chromatographed on a 32 × 5 cm column of SilicAR CC-7 Special adsorbent using 1:1 chloroform: hexane and chloroform as successive eluents. Isothiazolo [3,4-f][1,2,3,4,5]-pentathiepine-3-(N-methyl-N-butylcarboxamide) (1.59 g) of 98.9% purity (HPLC) has mass spectrum: m/e 324 $(M-S)^+$ and 292 $(M-S_2)^+$ and IR: νmax 1650 cm$^{-1}$ ($CONR_1R_2$).

EXAMPLE 10

Isothiazolo[3,4-f][1,2,3,4,5]pentathiepine-3-(N-phenylcarboxamide)

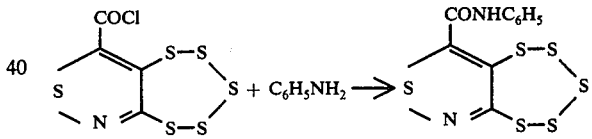

The method of Example 8A was used to prepare the acid chloride from 3 g of the carboxylic acid. The method of Example 5B was employed substituting a solution of 2 ml of aniline in 20 ml of dichloromethane for the dimethylamine. The crude pale yellow solid amide (1.62 g) was chromatographed on SilicAR CC-7 Special adsorbent using chloroform as the eluent. Isothiazolo[3,4-f][1,2,3,4,5]pentathiepine-3-(N-phenylcarboxamide) (0.32 g) of 99% purity (HPLC) was obtained from one of the chromatography fractions. It has IR: νmax 3400 (NH), 1660 (CONH) and 1610 cm$^{-1}$ (aromatic) and mp 157°–161° C. dec.

EXAMPLE 11

| Dust | |
|---|---|
| Isothiazolo[3,4-f][1,2,3,4,5]pentathiepine-3-carboxamide | 10% |
| Attapulgite | 10% |
| Talc | 80% |

The active ingredient is blended with attapulgite and then passed through a hammer mill to produce particles substantially all below 200 microns. The ground concentrate is then blended with powdered talc until homogeneous. All compounds of the invention may be formulated in like manner.

EXAMPLE 12

| | |
|---|---|
| Isothiazolo[3,4-f][1,2,3,4,5]pentathiepine-3-carbonitrile | 1% |
| technical xylenes | 99% |

The ingredients are stirred to produce a solution which is useful for treating wood or cloth.

EXAMPLE 13

| | |
|---|---|
| Oil Suspension | |
| Isothiazolo[3,4-f][1,2,3,4,5]pentathiepine-3-carbonitrile | 25% |
| Polyoxyethylene sorbitol hexaoleate | 5% |
| Highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 14

| | |
|---|---|
| Solution | |
| Isothiazolo[3,4-f][1,2,3,4,5]pentathiepine-3-carbonitrile | 30% |
| Dimethylformamide | 70% |

The ingredients are combined and stirred to produce a solution, which can be used for low volume applications.

EXAMPLE 15

| | |
|---|---|
| Aqueous Suspension | |
| Isothiazolo[3,4-f][1,2,3,4,5]pentathiepine-3-carboxamide | 50.0% |
| Polyacrylic acid thickener | 0.3% |
| Dodecylphenol polyethylene glycol ether | 0.5% |
| Disodium phosphate | 1.0% |
| Monosodium phosphate | 0.5% |
| Polyvinyl alcohol | 1.0% |
| Pentachlorophenol | 0.4% |
| Water | 46.3% |

EXAMPLE 16

| | |
|---|---|
| Wettable Powder | |
| Isothiazolo[3,4-f][1,2,3,4,5]pentathiepine-3-carboxamide | 80% |
| sodium dioctyl sulfosuccinate | 1% |
| Methyl cellulose | 3% |
| Synthetic amorphous silica | 3% |
| Kaolinite | 13% |

The ingredients are thoroughly blended, passed through an air mill to produce an average particle size under 15 microns, reblended, and sifted through a U.S.S. #50 sieve before packaging.

All compounds of the invention may be formulated in the same manner.

EXAMPLE 17

| | |
|---|---|
| High Strength Concentrate | |

| | |
|---|---|
| -continued | |
| Isothiazolo[3,4-f][1,2,3,4,5]pentathiepine-3-carbonitrile | 99% |
| Trimethylnonyl polyethylene glycol ether | 1% |

The surfactant is sprayed upon the active ingredient in a blender and the mixture sifted through a U.S.S. #50 sieve prior to packaging. The concentrate may be formulated further for practical use.

EXAMPLE 18

| | |
|---|---|
| Wettable Powder | |
| Isothiazolo[3,4-f][1,2,3,4,5]pentathiepine-3-N-(1-methylethyl)carboxamide | 50% |
| sodium alkylnaphthalene sulfonate | 2% |
| low viscosity methylcellulose | 2% |
| diatomaceous earth | 46% |

The ingredients are blended, coarsely hammer-milled and then air-milled to produce particles practically all below 10 microns in diameter. The product is reblended before packaging.

EXAMPLE 19

Tomato seedlings were sprayed to the point of run-off with a dispersion consisting of acetone, water, a surfactant and isothiazolo[3,4-f][1,2,3,4,5]pentathiepine-3-carbonitrile or isothiazolo[3,4-f][1,2,3,4,5]pentathiepine-3-carboxamide at a concentration of 100 ppm active ingredient. Treated and untreated plants were inoculated the next day with a spore suspension of the tomato late blight fungus (*Phytophthora infestans*) and incubated at 20° C in a saturated humidity for 24 hours. Disease ratings were made after 5 days in the greenhouse by a visual estimate of the percentage of diseased foliage. The untreated plants were killed by the fungus infections whereas the plants treated with the compounds of this invention had only an occasional lesion and were rated 70 to 80 percent disease control.

EXAMPLE 20

Two-week-old Straight Eight variety cucumber plants were sprayed uniformly to the point of run-off with a dispersion consisting of acetone, water, a surfactant and isothiazolo[3,4-f][1,2,3,4,5]pentathiepine-3-carbonitrile at 80 ppm. The following day all plants were inoculated with a distilled water suspension of powdery mildew (*Erysiphe cichoracearum*) conidia. After 8 days of incubation in the greenhouse, disease ratings were made by a visual estimate of the percentage of the inoculated leaf area that was diseased.

Powdery mildew was controlled at least 99 percent on treated plants, whereas the leaves on untreated cucumbers were about 95 percent covered with mildew.

EXAMPLE 21

Apple seedlings, trained to a single shoot, were sprayed to the point of run-off with a dispersion of acetone, water, a surfactant and isothiazolo[3,4-f][1,2,3,4,5]pentathiepine-3-carbonitrile at 80 ppm and 16 ppm. Treated and untreated plants were inoculated the same day with a suspension of cedar apple rust (*Gymnosporangium juniperi-virginianae*) spores and incubated at 20° C in saturated humidity for 24 hours. Disease ratings were made after 12 days in the greenhouse by counting the number of lesions on susceptible leaves. Untreated plants had an average of 20 lesions per leaf, but all trees treated with the compound of this invention were completely free of disease.

EXAMPLE 22

Apple seedlings, trained to a single shoot, were sprayed uniformly to the point of run-off with a dispersion consisting of acetone, water, a surfactant and the compounds listed below at 80, 16, and 3 ppm. Plants were inoculated the next day with a suspension of apple scab (*Venturia inaequalis*) conidia and incubated at 20° C in saturated humidity for 24 hours. Disease ratings were made, after 12 days in the greenhouse, by a visual estimate of the percentage of the inoculated leaf area that was diseased. A summary of readings, based on four replicate plants for each treatment, is shown below.

|  | Percent Apple Scab Control | | |
| --- | --- | --- | --- |
|  | 80 ppm | 16 ppm | 3 ppm |
| Isothiazolo[3,4-f][1,2,3,4,5]-pentathiepine-3-carbonitrile | 100 | 99 | 83 |
| Isothiazolo[3,4-f][1,2,3,4,5]-pentathiepine-3-carboxamide | 74 | 20 | 15 |

EXAMPLE 23

In an apple scab curative test, apple seedlings were first inoculated with a suspension of apple scab (*Venturia inaequalis*) conidia. The plants were immediately placed in a humidity chamber for 24 hours, then removed to the greenhouse for 24 hours. The infected plants were then sprayed with a dispersion of acetone, water, a small amount of surfactant and the compound listed below at 400, 80 and 16 ppm. The plants were returned to the humidity chamber for 24 hours and then removed to the greenhouse for 8 days whereupon disease intensity ratings were taken by a visual estimate of the percentage of inoculated leaf area that was diseased. The results in the table indicate percentage control when the treated plants are compared with plants not sprayed with the compound.

|  | Percent Apple Scab Control | | |
| --- | --- | --- | --- |
|  | 400 ppm | 80 ppm | 16 ppm |
| Isothiazolo[3,4-f][1,2,3,4,5]-pentathiepine-3-carbonitrile | 99 | 95 | 89 |

EXAMPLE 24

Sugar-beet seedlings were sprayed to the point of run-off with a dispersion of acetone, water, a surfactant and isothiazolo[3,4-f][1,2,3,4,5]pentathiepine-3-carbonitrile at 125 ppm. Treated and untreated plants were inoculated the next day with a suspension of leaf spot (*Cercospora beticoli*) conidia and incubated in saturated humidity for 3 days. Disease ratings were made after 18 days in the greenhouse by counting the number of lesions on susceptible leaves. Untreated plants had an average of 84 lesions per leaf, but the plants treated with the compound of this example had only a few lesions and the disease was 95 percent controlled.

EXAMPLE 25

Strips of "eight ounce" cotton duck were soaked in a 1 percent solution of isothiazolo[3,4-f][1,2,3,4,5]pentathiepine-3-carbonitrile in Stoddard solvent for 5 minutes. Similar strips were soaked in Stoddard solvent. All strips were air dried and placed in a container of moist, biologically-active soil. After 14 days all strips of cotton duck treated only with Stoddard solvent were disintegrated by the rotting action of a mixture of soil microorganisms. The strips treated with the above compound of this invention still retained full tensile strength and showed no signs of rotting after 70 days of exposure in the soil.

What is claimed is:

1. A compound of the formula

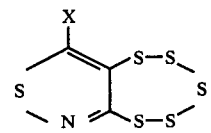

wherein
X is cyano or

Q is Cl, —OR$_1$, —SR$_1$ or —NR$_2$R$_3$;
R$_1$ is hydrogen, alkyl of 1-2 carbon atoms;
R$_2$ is hydrogen or methyl; and
R$_3$ is hydrogen, alkyl of 1-4 carbon atoms or phenyl, with the proviso that (a) when R$_2$ is hydrogen, R$_3$ is hydrogen or alkyl of 1-3 carbon atoms or phenyl and (b) when Q is SR$_1$, R$_1$ is not hydrogen.

2. The compound of claim 1 wherein X is cyano or

and Q is —NR$_2$R$_3$.

3. The compound of claim 1 wherein X is cyano or

Q is —NR$_2$R$_3$ and R$_3$ is hydrogen or alkyl of 1-3 carbon atoms.

4. The compound of claim 1, isothiazolo[3,4-f][1,2,3,4,5]pentathiepine-3-carbonitrile.

5. The compound of claim 1, isothiazolo[3,4-f][1,2,3,4,5]pentathiepine-3-carboxamide.

6. The compound of claim 1, isothiazolo[3,4-f][1,2,3,4,5]pentathiepine-3-[N-(1-methylethyl)carboxamide].

7. A fungicidal composition consisting essentially of a fungicidally effective amount of a compound of the formula

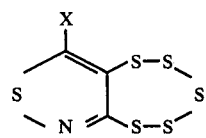

wherein
X is cyano or

Q is —OR$_1$, —SR$_1$ or —NR$_2$R$_3$;
R$_1$ is alkyl of 1–2 carbon atoms;
R$_2$ is hydrogen or methyl;
R$_3$ is hydrogen, alkyl of 1–4 carbon atoms or phenyl; with the proviso that when R$_2$ is hydrogen, R$_3$ is hydrogen or alkyl of 1–3 carbon atoms or phenyl, and at least one of (a) an inert diluent and (b) a surface active agent.

8. The composition of claim 7 wherein X is cyano or

and Q is —NR$_2$R$_3$.

9. The composition of claim 7 wherein X is cyano or

Q is —NR$_2$R$_3$ and R$_3$ is hydrogen or alkyl of 1–3 carbon atoms.

10. The composition of claim 7 wherein the compound is isothiazolo[3,4-f][1,2,3,4,5]pentathiepine-3-carbonitrile.

11. The composition of claim 7 wherein the compound is isothiazolo[3,4-f][1,2,3,4,5]pentathiepine-3-carboxamide.

12. The composition of claim 7 wherein the compound is isothiazolo[3,4-f][1,2,3,4,5]pentathiepine-3-[N-(1-methylethyl)carboxamide].

13. A method for controlling fungi consisting essentially of applying to the area to be protected a fungicidally effective amount of a compound of the formula

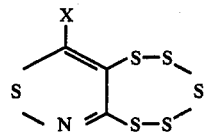

wherein
X is cyano or

Q is —OR$_1$, —SR$_1$ or —NR$_2$R$_3$;
R$_1$ is alkyl of 1–2 carbon atoms;
R$_2$ is hydrogen or methyl;
R$_3$ is hydrogen, alkyl of 1–4 carbon atoms or phenyl, with the proviso that when R$_2$ is hydrogen, R$_3$ is hydrogen or alkyl of 1–3 carbon atoms or phenyl.

14. The method of claim 13 wherein X is cyano or

and Q is —NR$_2$R$_3$.

15. The method of claim 13 wherein X is cyano or

Q is —NR$_2$R$_3$ and R$_3$ is hydrogen or alkyl of 1–3 carbon atoms.

16. The method of claim 13 wherein the compound is isothiazolo[3,4-f][1,2,3,4,5]pentathiepine-3-carbonitrile.

17. The method of claim 13 wherein the compound is isothiazolo[3,4-f][1,2,3,4,5]pentathiepine-3-carboxamide.

18. The method of claim 13 wherein the compound is isothiazolo[3,4-f][1,2,3,4,5]pentathiepine-3-[N-(1-methylethyl)carboxamide].

* * * * *